(12) United States Patent
Maykut et al.

(10) Patent No.: US 8,129,577 B2
(45) Date of Patent: Mar. 6, 2012

(54) PROCESS AND SYSTEM FOR PROVIDING ACETYLENE

(75) Inventors: Timothy John Maykut, Bethlehem, PA (US); Suhas Narayan Ketkar, Allentown, PA (US); Benjamin James Arthur Inman, Basingstoke (GB); John Irven, Somerset (GB); Eugene Joseph Karwacki, Jr., Orefield, PA (US); Neil Alexander Downie, Hampshire (GB)

(73) Assignee: Air Products and Chemicals, Inc., Allentown, PA (US)

( * ) Notice: Subject to any disclaimer, the term of this patent is extended or adjusted under 35 U.S.C. 154(b) by 312 days.

(21) Appl. No.: 12/554,052

(22) Filed: Sep. 4, 2009

(65) Prior Publication Data

US 2010/0069689 A1 Mar. 18, 2010

Related U.S. Application Data

(60) Provisional application No. 61/097,352, filed on Sep. 16, 2008.

(51) Int. Cl.
*B65B 1/04* (2006.01)

(52) U.S. Cl. .............. 585/899; 141/3; 141/20; 585/809; 585/820

(58) Field of Classification Search ........................ None
See application file for complete search history.

(56) References Cited

U.S. PATENT DOCUMENTS

| | | | |
|---|---|---|---|
| 4,863,493 A | 9/1989 | Kotani et al. | |
| 5,032,619 A | 7/1991 | Frutin et al. | |
| 5,139,057 A | 8/1992 | Benedetti | |
| 6,406,519 B1 | 6/2002 | Tom et al. | |
| 6,953,068 B2 | 10/2005 | Hord, III et al. | |
| 2008/0242912 A1* | 10/2008 | Letessier et al. | 585/821 |

FOREIGN PATENT DOCUMENTS

| | | |
|---|---|---|
| EP | 0 660 029 A1 | 6/1995 |
| EP | 0 856 698 A2 | 8/1998 |
| EP | 1 193 309 A1 | 4/2002 |
| EP | 0 916 891 B1 | 10/2006 |
| JP | 62019539 | 1/1987 |
| JP | 63295518 A2 | 1/1988 |
| WO | 0001615 A1 | 1/2000 |
| WO | 2004089859 A2 | 10/2004 |
| WO | 2008012231 A2 | 1/2008 |

OTHER PUBLICATIONS

Ed Warzyniec, Safe handling of compressed gases and cryogenic liquids, Chemical Health & Safety, May/Jun. 2000, pp. 34-36.

* cited by examiner

*Primary Examiner* — Tam M Nguyen

(74) *Attorney, Agent, or Firm* — Rosaleen P. Morris-Oskanian; Joseph D. Rossi

(57) ABSTRACT

A system and a process for providing acetylene, preferably at a high purity level (e.g., comprising 100 parts per million ("ppm"), or 10 ppm, or 1 ppm, or 100 parts per billion ("ppb"), or 10 ppb, or 1 ppb or less of solvent), to a point of use, such as a semiconductor manufacturing process, is described herein. In one aspect, there is provided a process for providing a process for providing a high purity acetylene comprising 100 ppm or less solvent to a point of use comprising: providing an acetylene feed stream comprising acetylene and solvent at a temperature ranging from 20° C. to −50° C.; and introducing the acetylene feed stream to a purifier at a temperature ranging from −50° C. to 30° C. to remove at least a portion of the solvent contained therein and provide the high purity acetylene.

5 Claims, 9 Drawing Sheets

PROCESS AND SYSTEM FOR PROVIDING ACETYLENE

CROSS-REFERENCE TO RELATED APPLICATIONS

This application claims the benefit of U.S. Provisional Application No. 61/097,352, filed 16 Sep. 2008.

BACKGROUND OF THE INVENTION

Described herein is a system and a process for providing acetylene, preferably at a high purity level (e.g., comprising 100 parts per million ("ppm"), or 10 ppm, or 1 ppm, or 100 parts per billion ("ppb"), or 10 ppb, or 1 ppb or less of solvent), to a point of use. More specifically, described herein is a delivery system that provides a continuous flow of virtually solvent free (e.g., comprising 100 ppm or below of solvent) acetylene for use in semiconductor manufacturing.

Semiconductor manufacturers are using acetylene ($C_2H_2$) for certain applications such as, for example, hard (carbon-rich) mask coating processes. Acetylene is typically provided at a point of use in a cylinder that can be delivered to the manufacturer and then removed and refilled. Acetylene, however, presents many problems in handling and delivery. Acetylene is the most thermodynamically unstable common gas, is highly flammable, has a very wide explosive range (from 2% to 80% in air), and under pressure and certain conditions can decompose with explosive force. With regard to the latter, pure acetylene under pressure as low as 6 psig can violently decompose under certain conditions. Acetylene cylinders are designed to avoid the aforementioned problems with decomposition and flammability by providing a porous material that is saturated with acetone or another suitable solvent into which the acetylene is dissolved. The combination of the porous mass and solvent allows acetylene to be stored safely in cylinders at a pressure of about 250 psig. However, the acetone solvent can introduce up to 10% acetone vapor which can contaminate the manufacturing process, end product, or both.

Accordingly, there is a need in the art to provide a system and a process for the safe handling and delivery of acetylene to a point of use wherein the acetylene is delivered at a high purity level particularly for semiconductor manufacturing processes.

BRIEF SUMMARY OF THE INVENTION

Described herein is a process and system for providing acetylene, preferably at a high purity level (e.g., comprising 100 parts per million ("ppm"), or 10 ppm, or 1 ppm, or 100 parts per billion ("ppb"), or 10 ppb, or 1 ppb or less of solvent) to a point of use. In one aspect, there is provided a process for providing a high purity acetylene comprising 100 ppm or less solvent to a point of use comprising: providing an acetylene feed stream comprising acetylene and solvent at a temperature ranging from 20° C. to −50° C.; and introducing the acetylene feed stream to a purifier at a temperature ranging from −50° C. to 30° C. to remove at least a portion of the solvent contained therein and provide the high purity acetylene. In certain embodiments, the feed stream enters the purifier at room temperature (e.g., approximately 25° C.).

In another aspect, there is provided a process for providing a high purity acetylene comprising 100 ppm or less of a solvent comprising dimethylformamide to a point of use comprising: reducing the temperature of an acetylene feed stream comprising acetylene and the solvent to a range of from 20° C. to −50° C. to provide a high purity acetylene; and introducing the high purity acetylene to a point of use.

In a further aspect, there is provided a system to provide a purified acetylene fluid stream to a point of use in, for example, a semiconductor manufacturing site. In one aspect, the system for providing a high purity acetylene comprising 100 ppm or less solvent to a point of use comprises: a storage vessel that houses an acetylene feed steam comprising acetylene and solvent; a cooling system that maintains the storage vessel and provides the acetylene feed stream at a temperature ranging from 20° C. to −50° C.; and a purifier in fluid communication with the storage vessel wherein the acetylene feed stream is introduced into the purifier at a temperature ranging from −50° C. to 30° C. to remove at least a portion of the solvent contained therein and provide the high purity acetylene.

DETAILED DESCRIPTION OF THE INVENTION

Figure 1:
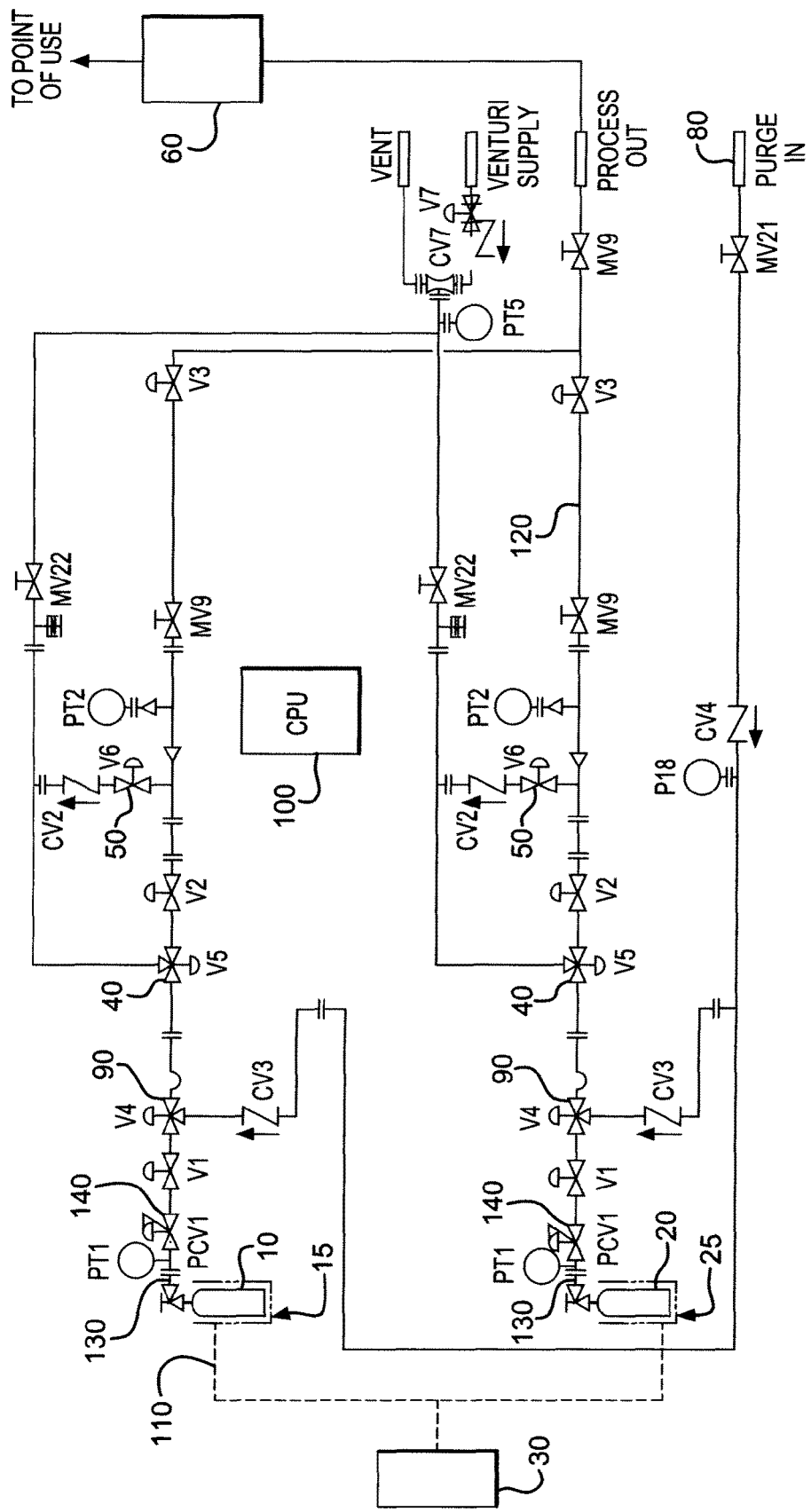
FIG. 1 provides an example of an embodiment of the system described herein for providing high purity acetylene.

Described herein is a system and a method that provides acetylene ($C_2H_2$) at a high purity level (e.g., comprising 100 parts per million ("ppm"), or 10 ppm, or 1 ppm, or 100 parts per billion ("ppb"), or 10 ppb, or 1 ppb or less of solvent), to a point of use such as, for example, semiconductor manufacturing equipment such as, but not limited to, an ion implanter, an etch chamber, a chemical vapor deposition reactor, or an atomic layer deposition reactor.

As previously mentioned, acetylene storage cylinders or vessels are designed to avoid the problems with decomposition and flammability by providing a porous material that is saturated with acetone and/or another suitable solvent into which the acetylene is dissolved. Examples of solvents that are used within acetylene storage cylinders or vessels include, but are not limited to, acetone, dimethylformamide (DMF), N-methyl-pyrrolidone, and mixtures thereof. The system and process described herein avoids the problems associated with the prior art by providing the acetylene feed stream at a temperature range of from 20° C. from −50° C. by cooling the storage vessel or cylinder to the temperature range at the storage source through the use of a chiller system or other means. The temperature range of 20° C. to −50° C. at which the acetylene feed stream is provided at may include any one or more of the following endpoints: 20° C., 15° C., 10° C., 5° C., 0° C., −5° C., −10° C., −15° C., −20° C., −25° C., −30° C., −35° C., −40° C., −45° C., or −50° C. Examples of certain temperature ranges for the acetylene storage vessel includes, but are not limited to, 0° C. to −35° C., 20° C. to −5° C., or 10° C. to −15° C. The particular temperature range that the acetylene feed stream is provided at may vary depending upon the vapor pressure of the one or more solvents contained therein. At reduced temperatures, the vapor pressure of the solvent will be so low that there will be minimal carryover of the solvent into the acetylene feed stream. For example, in embodiments wherein the acetylene is dissolved in the solvent acetone, when the acetylene feed stream is delivered from the storage vessel at a temperature of −20° C., more of the solvent acetone remains within the storage vessel because its vapor pressure is 0.02654 bar. In other embodiments wherein the acetylene is dissolved in the solvent DMF, when the acetylene feed stream is delivered from the storage vessel at a temperature of −20° C., more of the solvent DMF remains within the storage vessel because its vapor pressure is 0.00019 bar. In the latter embodiment, the acetylene feed stream comprising the solvent DMF, after being reduced to a temperature such as −20°, may be sufficiently pure enough to supply to the point of use without having to pass through one or more purifiers. Table I below provides the temperature of dispensing acetylene from the storage vessel comprising DMF and the vapor pressure in bars at certain dispensing temperatures within the range.

TABLE I

| Temperature of Dispensing Acetylene from Storage Vessel (° C.) | Vapor Pressure of DMF solvent (bars) | Vapor Pressure of acetone solvent (bars) |
|---|---|---|
| −20° C. | 0.00019 | 0.02654 |
| −30° C. | 0.00008 | 0.01382 |
| −40° C. | 0.00003 | 0.00681 |
| −50° C. | 0.00001 | 0.00314 |

Unlike gas phase cooling methods for acetone removal, the system and process described herein may also reduce the likelihood of generating liquid acetylene and may also eliminate the need for the customer to handle the solvent contained within the acetylene storage vessel.

The system and process described herein also provides one or more purifiers that are used prior to providing the purified acetylene fluid stream at its point of use. The term "fluid" as used herein denotes liquid as well as gaseous, sublimed solids, and variations thereof of a substance. Examples of purifiers that may be used within the system and process include, but are not limited to, activated carbon, molecular sieves, silica gel, zeolite, and combinations thereof. The one or more purifiers act to remove the remaining residual solvent that may be present in the acetylene feed stream. Because the acetylene feed stream entering the purifier is at a lower temperature, the "loading" on the purifier is lessened because less solvent will be present within the acetylene feed stream when it enters the purifier and therefore less solvent needs to be removed from the acetylene feed stream. This may reduce the overall cost of ownership because there is less solvent carry-over, thereby reducing the size and capacity of the purifier. Further, the purifier(s) in the system and method described herein can operate at temperature range of from about −50° C. to 30° C. The temperature range of −50° C. to 30° C. at which the acetylene feed stream enters the purifier may include any one or more of the following endpoints: 30° C., 25° C., 20° C., 15° C., 10° C., 5° C., 0° C., −5° C., −10° C., −15° C., −20° C., −25° C., −30° C., −35° C., −40° C., −45° C. or −50° C. Examples of certain temperature ranges for the acetylene storage vessel includes, but are not limited to, 0° C. to −15° C., 20° C. to −5° C., or 10° C. to 30° C. In one embodiment, the acetylene feed stream enters the purifier at room temperature (e.g., 25° C.). In another embodiment, such as when the acetylene feed stream comprises the solvent DMF, the acetylene feed stream when reduced to a certain temperature may not need to be introduced into one or more purifiers.

FIG. 1 provides an example of an embodiment of the system described herein for providing high purity acetylene fluid to a point of use. In this embodiment, the system and process provides consistent and uninterrupted solvent-free delivery of acetylene to the semiconductor manufacturing process by comprising at least two cylinders 10 and 20 that are designed to be fully redundant. An acetylene feed stream is supplied to the down-stream process from a first or primary cylinder or storage vessel 10 whereas the second or secondary cylinder or storage vessel 20 is provided as a stand-by or back-up cylinder. For example, if the acetylene feed stream is interrupted by the first cylinder by, for example, volume reduction, equipment failure, etc., the acetylene feed stream automatically switches (auto-crossover) to the second cylinder. In other embodiments, a plurality of acetylene storage vessels may be used to provide an uninterrupted flow of the acetylene feed stream. The system further comprises a central processing unit ("CPU") 100 that is in electrical communication with one or more of the following system components such as the various pressure control valves ("PCV"), level sensors, heat sensors, safety valves, cooling system, and the like. CPU 100 can also control the temperature of primary and secondary cylinders 10 and 20 and monitor delivery pressure, cylinder pressure and cylinder weight. For example, low cylinder weight and pressure in primary cylinder 10 may trigger auto-crossover to the stand-by or secondary cylinder 20 at predetermined setpoints which are monitored by CPU 100. In this embodiment, the flow of process gas to the semiconductor process is not interrupted as the operator can now change the empty first cylinder 10 while flow is supplied to the manufacturing process from the second cylinder 20.

Cylinders 10 and 20 comprise a acetylene feed stream comprising acetylene and at least one solvent selected from but are not limited to, acetone, dimethylformamide (DMF), N-methyl-pyrrolidone, and mixtures thereof. The acetylene is dissolved into the solvent. In certain embodiments, the cylinders may also comprise a porous media, such as but not limited to calcium silicate, which is used to soak up the solvent contained therein. The cylinders are stored at a pressure of up to 250 pounds per square inch (psi). For safety reasons, the delivery pressure is not to exceed 15 psig. Cylinders 10 and 20 are also equipped with a flash arrestor 130 that is designed to prevent a rapid release of pressure if, for example, cylinders 10 and 20 fall over or are damaged. In certain embodiments, cylinders 10 and 20 are also equipped with a pressure regulator 140 such as that depicted in pending European Patent Application No. 916891 which is assigned to the assignee of the present application. In the embodiment shown in FIG. 1, cylinders 10 and 20 are chilled to a temperature range of from 0° C. to −20° C. by recirculating chiller 30. In one particular embodiment, cylinders 10 and 20 are chilled using cylinder cooling jacket 15 that are connected to a chiller via lines 110. However, it is envisioned that other means can be employed to maintain cylinders 10, 20 or both at the desired temperature range. The system depicted in FIG. 1 contains regulators, flow meters, valves, hose, and pipe lines that are compatible with the safe storage and handling of acetylene containing fluids at the aforementioned temperature and pressure ranges. The system depicted in FIG. 1 is also designed for automated purging and venting for high purity operation. The purge line 80 is connected through V4 90 and the vents are connected through V5 40 and V6 50. The automated purge cycles are initiated and monitored by CPU 100 controller to switch between periods of positive pressure purge gas flow and evacuation to negative pressure via the vacuum venturi. Pressure transducers and an excess flow switch within the system depicted in FIG. 1 monitor process conditions to provide alarms and shutdowns during system upset conditions.

In the system depicted in FIG. 1, an acetylene feed stream from either cylinder 10 or 20 travels through a purifier 60 at a temperature ranging from about −50° C. to 30° C., or about ~25° C. and a pressure of up to 15 psi to provide a purified acetylene fluid stream. In the embodiment of the system depicted in FIG. 1, the acetylene-containing feed stream is at room temperature by the time it reaches the purifier because piping from the system to the point of use is not insulated. Further, in the embodiment of the system depicted in FIG. 1, the temperature of the delivered acetylene is not critical to the end use process. However, it is envisioned that insulation of the piping or other means of controlling the temperature of the acetylene feed stream prior to or upon entry to the purifier can be used. While the embodiment shown in FIG. 1 depicts the use of one purifier, it is understood that the system can be modified to use a plurality of purifiers (e.g., two or more purifiers). Further, the system and process described herein can also allow a regeneration step to allow the residual solvent within the purifier to be removed. Examples of purifiers that may be used within the system and process include, but are not limited to, activated carbon, molecular sieves, silica gel, zeolite, and combinations thereof. One particular example of a purifier that can be used in the system and process described herein is the MICROTOOR® MC4500 provided by SAES Pure Gas, Inc. of San Luis Obispo, Calif. The acetylene-containing feed stream is passed through purifier 60 at a temperature of range from about −50° C. to 30° C., or alternatively about ~25° C. or room temperature, and a pressure of up to 15 psig to remove any residual solvent contained within the acetylene-containing feed. The purified acetylene fluid stream comprises 100 parts per million ("ppm"), or 10 ppm, or 1 ppm, or 100 parts per billion ("ppb"), or 10 ppb, or 1 ppb or less of solvent. After passing through purifier 60, the purified acetylene fluid stream flows out into point of use.

In another embodiment of the process and system described herein, the storage vessel comprising acetylene and a solvent is reduced to a temperature sufficient to allow the solvent to remain within the storage vessel due to it low vapor pressure thereby allowing a high purity acetylene fluid stream to be dispensed directly from the vessel and avoiding the need to introduce the fluid stream into one or more purifiers.

The system and process described herein provides at least one of the following advantages. The system and process described herein may provide a greater utilization of the acetylene cylinder volume. At room temperature (e.g., 25° C.), the acetylene utilization is approximately 50% of the total acetylene volume in the cylinder. At room temperature and greater than 50% utilization, the solvent carryover is so high that it is not usable in semiconductor manufacturing processes. It is believed that reducing the cylinder temperature may reduce the solvent vapor pressure to a level that allows greater utilization of the acetylene cylinder volume before the solvent reaches impractical levels. The system and process described herein may also reduce the amount of solvent that leaves the cylinder thereby increasing the number of times the cylinder can be refilled before more acetone has to be added to the cylinder. This reduces the overall cost of ownership, because customers are using more of the gas they purchase. Moreover, with greater utilization, there are fewer cylinder changes required, reducing the labor cost associated with providing acetylene.

The following examples are provided to further illustrate the system and method disclosed herein are not intended to limit it in any way.

Examples

The examples described herein use a acetylene feed stream provided from commercially available acetylene cylinders, having a nominal acetylene fill of 5 kg and using acetone as the solvent it is dissolved therein. The acetylene feed stream was continuously feed at a feed rate that ranged from 5 to 15 standard liters per minute (SPLM) but averaged a flow rate of 10 SPLM. Depending upon the temperature condition, the cylinders were fitted with a cylinder jacket and cooled using chiller manufactured by ThermoScientific Neslab. The acetylene feed stream from each cylinder flowed through a Mega-Torr purifier manufactured by SAES Getters, Lianate, Italy. Samples of the acetylene feed stream prior to and after entering the purifier were taken and analyzed for acetone content using either a Draeger Tube (manufactured by Draeger Safety, Inc. of Lubeck), Non Dispersive Infra Red (NDIR) (manufactured by ADC Gas Analysis Ltd. of Hoddesdon, England) or a Gas Chromatograph (GC) with a thermal Conductivity Detector (TCD) (manufactured by Agilent Technologies of Santa Clara, Calif.). The experiment was conducted until all of the acetylene within the cylinder was depleted such that it was not possible to sustain an average flow rate of 10 SLPM.

Figure 2:
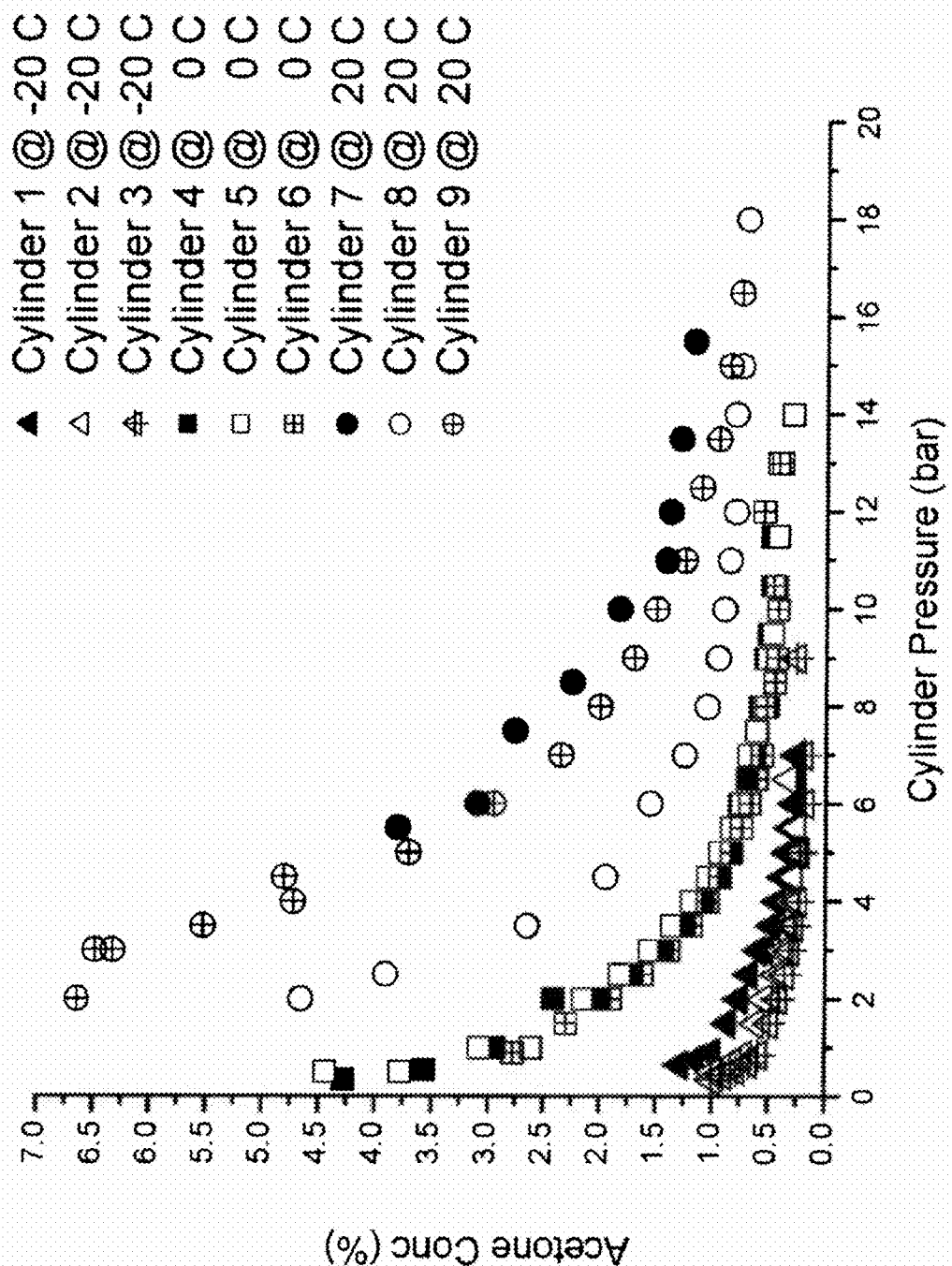
FIG. 2 provides a comparison of the acetone concentration versus cylinder pressure for 9 exemplary acetylene-containing cylinders at 3 different temperature conditions (e.g., −20° C., 0° C., and 20° C.).

The experiments were performed on three different cylinders each having the same storage volume at three different temperature conditions (e.g., 20° C., 0° C. and −20° C.). Experiments were performed on three different cylinders at each of the three temperatures in order to investigate the variability in the behavior of different cylinders. The results of the experiments are provided in FIG. 2. FIG. 2 shows that there is some variability in the results of the different cylinders kept at the same temperature. The variability results from the variability in the amount of acetone that is present within the cylinders. Typically, acetone is added to the acetylene cylinders after every 4 or 5 fills of acetylene. In between the refills of acetone, the amount of acetone in acetylene cylinders varies. As acetone is dispensed form the cylinder, the pressure in the cylinder decreases and the fractional concentration of acetone in the acetylene increases. The data in FIG. 2 also shows that as the temperature of the cylinder is decreased, the fractional concentration of acetone in the dispensed acetylene decreases.

Figure 3:
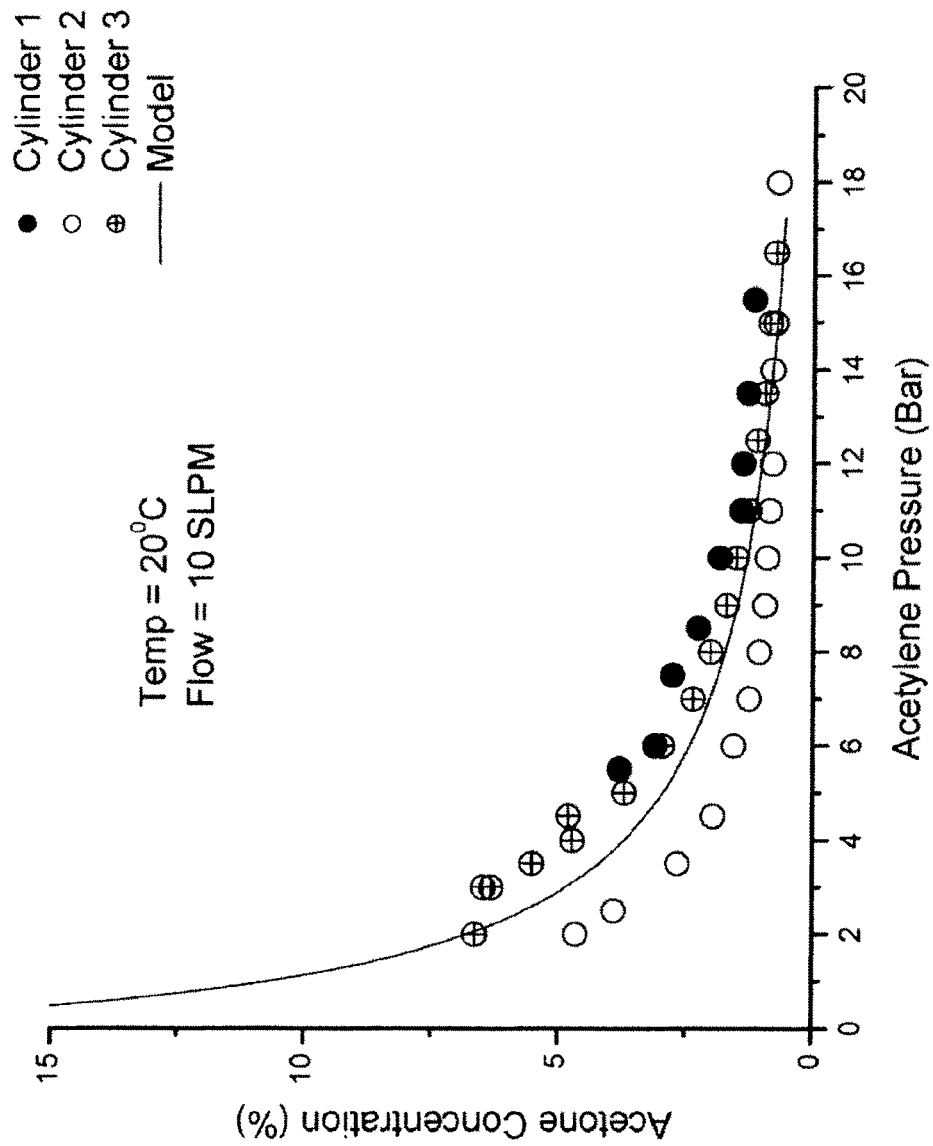
FIG. 3 illustrates the relationship between acetone concentration and acetylene pressure for 3 exemplary acetylene-containing cylinders at a temperature of 20° C. and a flow rate of 10 standard liters per minute (SPLM) with regard to a thermodynamic model.
Figure 4:
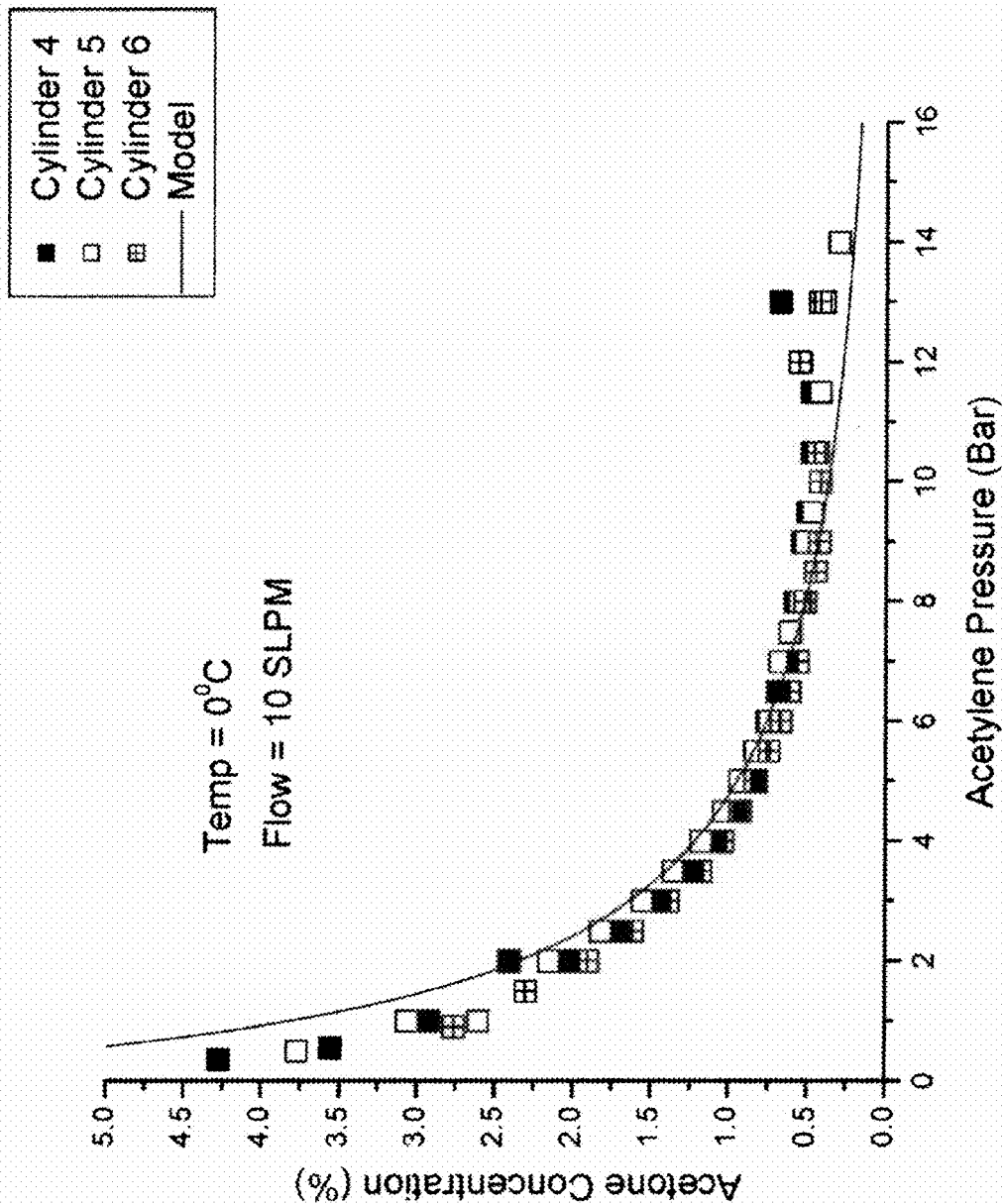
FIG. 4 illustrates the relationship between acetone concentration and acetylene pressure for 3 exemplary acetylene-containing cylinders at a temperature of 0° C. and a flow rate of 10 standard liters per minute (SPLM) with regard to a thermodynamic model.
Figure 5:
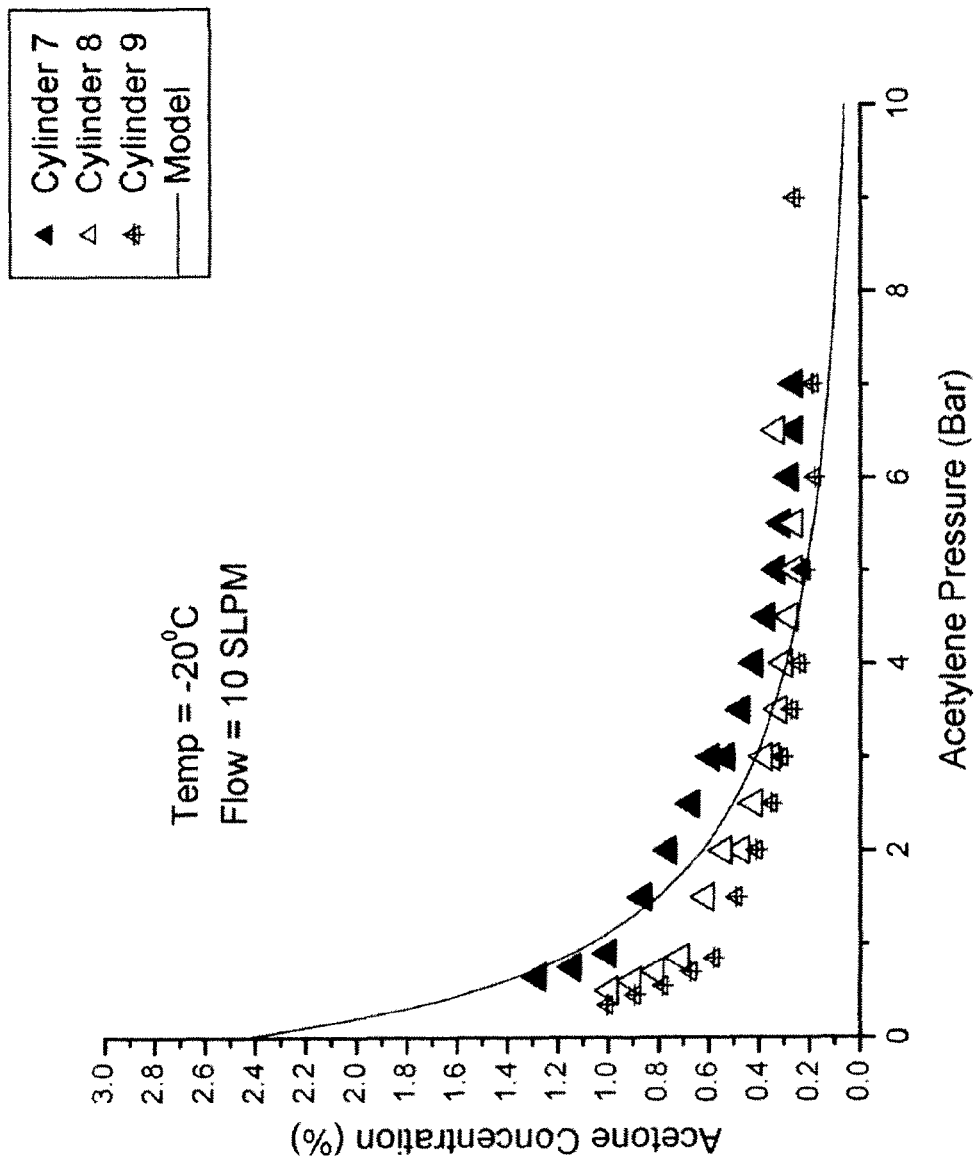
FIG. 5 illustrates the relationship between acetone concentration and acetylene pressure for 3 exemplary acetylene containing cylinders at a temperature of −20° C. and a flow rate of 10 standard liters per minute (SPLM) with regard to a thermodynamic model.

Thermodynamic modeling, using the temperature dependence of the solubility coefficients for acetylene in acetone, was performed to predict the fractional concentration of acetone in the dispensed acetylene and compared against the experimental data obtained at different cylinder temperatures (e.g., −20° C., 0° C., and 20° C.) and the results of this analysis are provided in FIGS. 3, 4, and 5. The acetylene solubility parameters in acetone and DMF were obtained from literature reviews and an internal CAPP computer modeling program was used to calculated the fractional concentrations. FIGS. 3, 4, and 5 show that the model predictions agree with the experimental data obtained.

Figure 6:
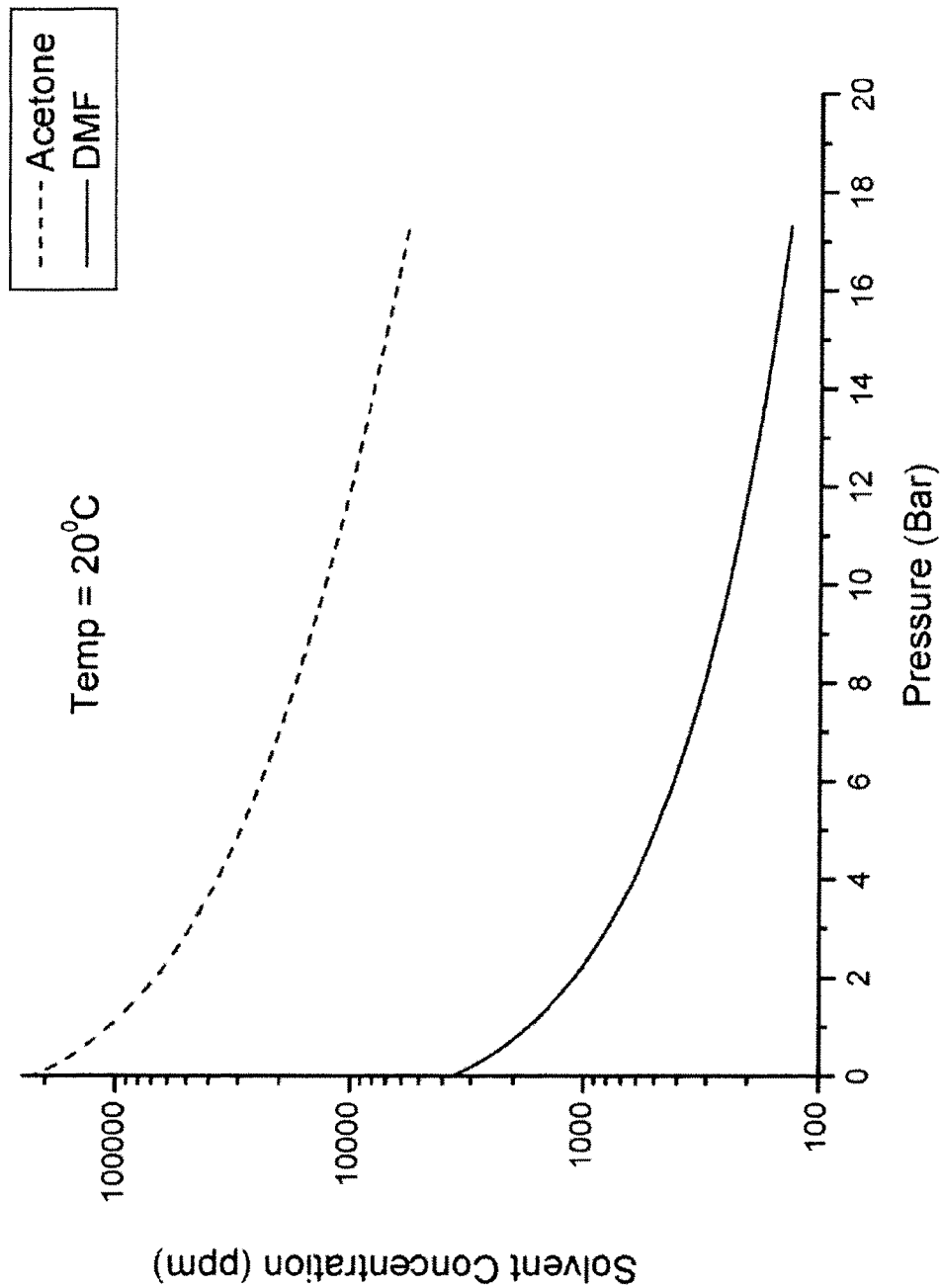
FIG. 6 provides the comparison of solvent concentration in parts per million of the solvent acetone in the acetylene-containing cylinder at a temperature of 20° C. against a thermodynamic model of an acetylene-containing cylinder containing dimethylformamide (DMF) at the same temperature.
Figure 7:
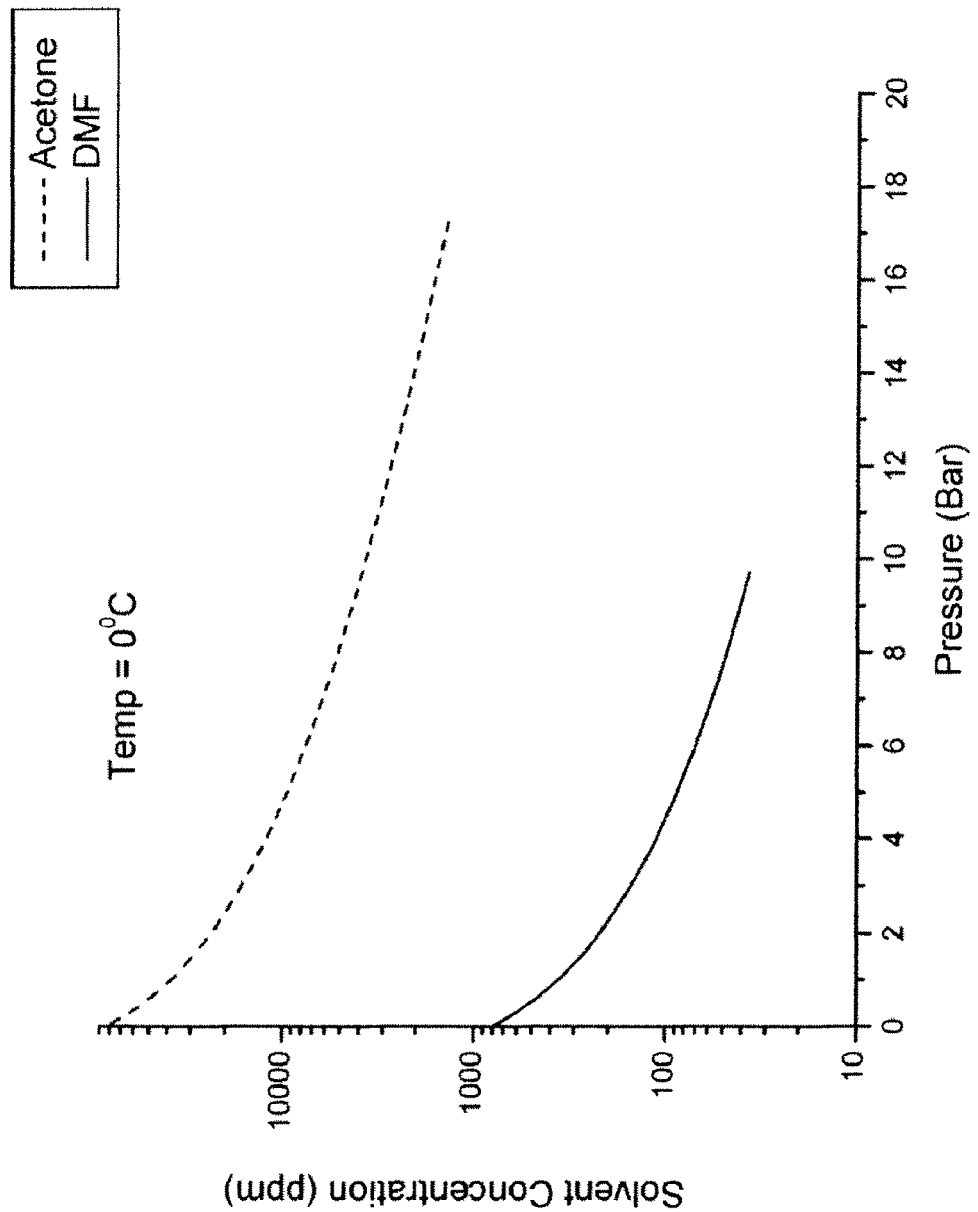
FIG. 7 provides the comparison of solvent concentration in parts per million of the solvent acetone in the acetylene-containing cylinder at a temperature of 0° C. against a thermodynamic model of an acetylene-containing cylinder containing dimethylformamide (DMF) at the same temperature.
Figure 8:
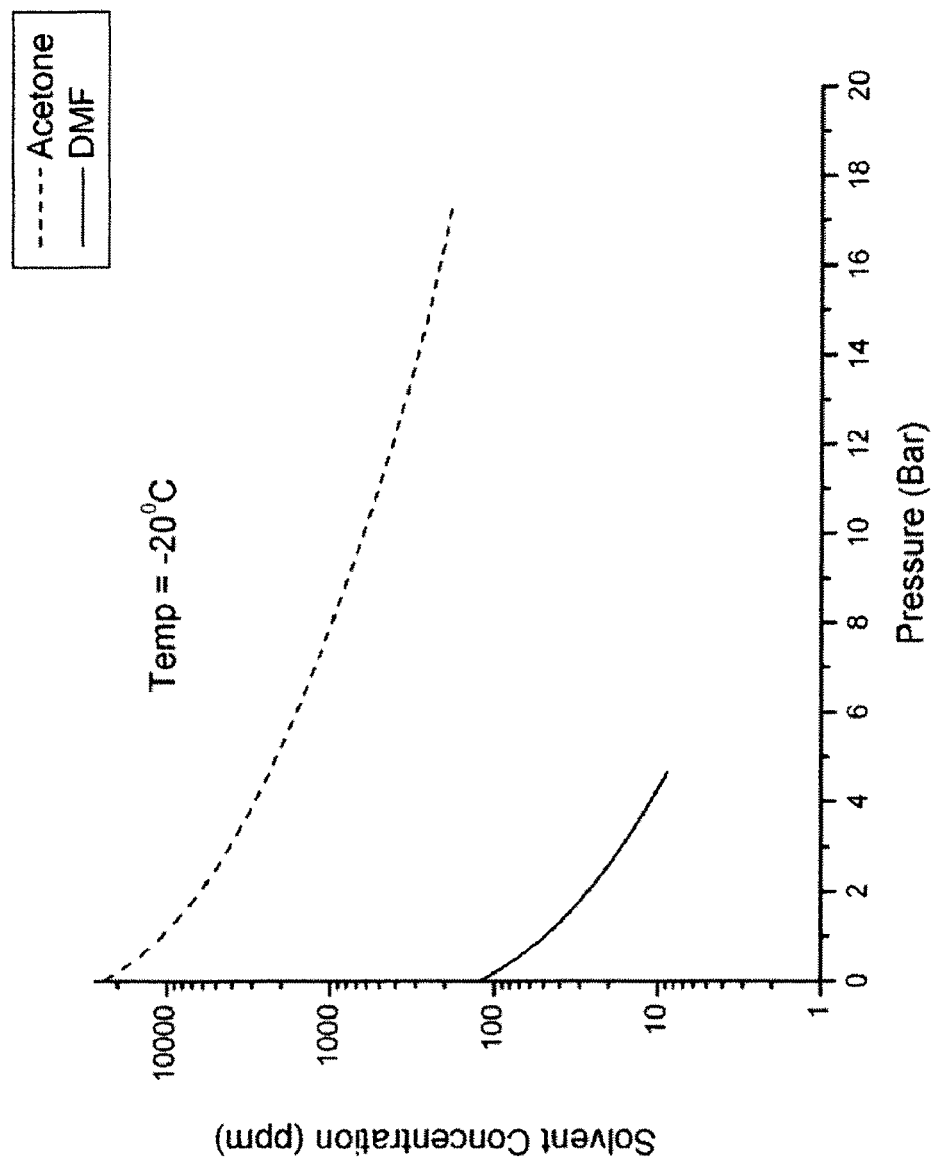
FIG. 8 provides the comparison of solvent concentration in parts per million of the solvent acetone in the acetylene-containing cylinder at a temperature of −20° C. against a thermodynamic model of an acetylene-containing cylinder containing dimethylformamide (DMF) at the same temperature.

Thermodynamic modeling was also performed using the temperature dependence for dimethylformide (DMF) as the solvent rather than acetone. The acetylene solubility parameters in acetone and DMF were obtained from literature reviews and an internal CAPP computer modeling program was used to calculated the fractional concentrations. The results of the thermodynamic model for cylinder temperatures of 20° C., 0° C., and −20° C. are shown in FIGS. 6, 7, and 8 and compared against the model predictions for acetone. The model predictions indicate that the lower vapor pressure of DMF or the fractional concentration of the solvent DMF in dispensed acetylene would be lower than when the solvent acetone is used.

Figure 9:
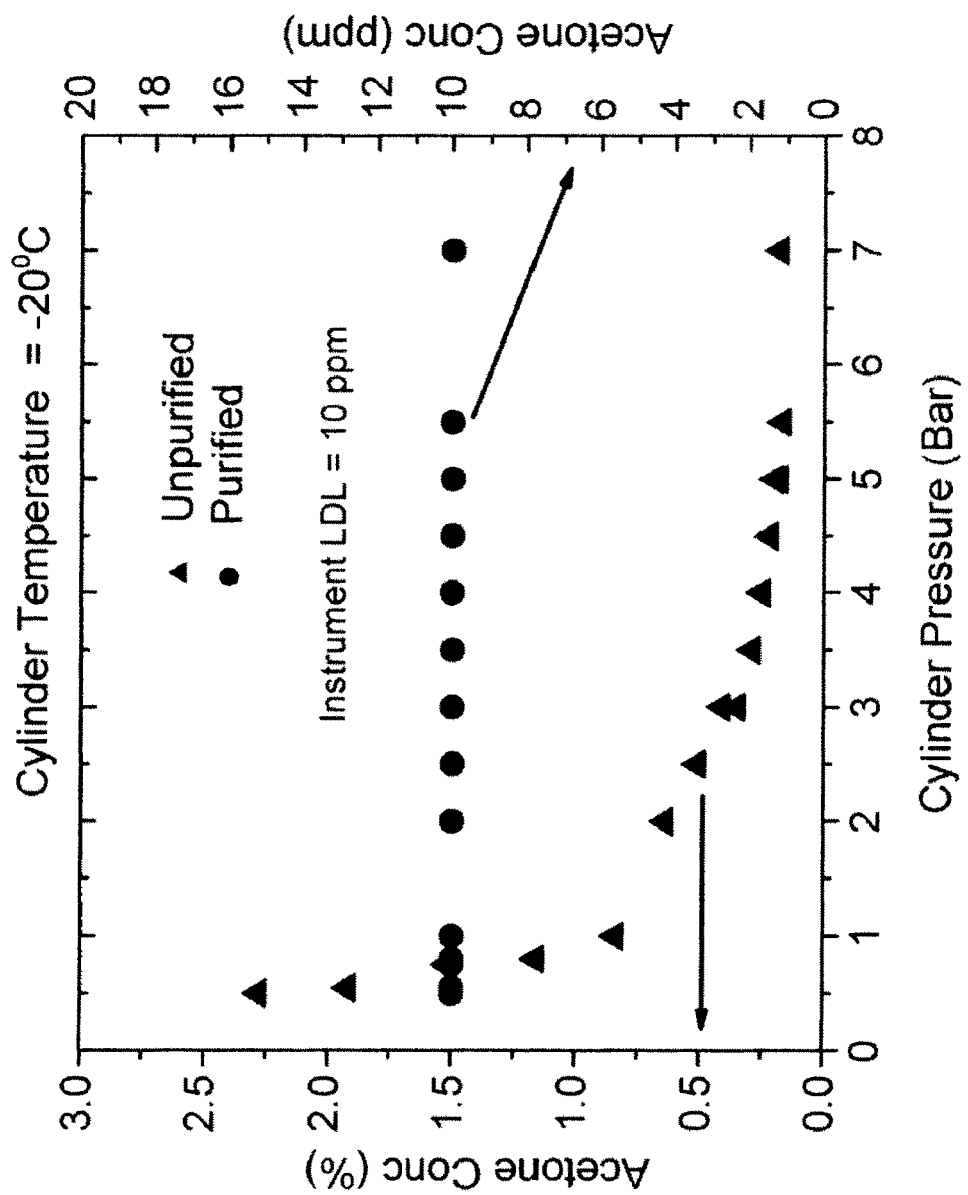
FIG. 9 compares the fractional concentration of acetone solvent in the acetylene-containing cylinder that is cooled to a temperature of −20° C. and either passed through a purifier or not passed through a purifier.

The use of a purifier further reduces the fractional concentration of the solvent in the acetylene. FIG. 9 shows the comparison of the results of the experiments performed using acetone as a solvent that is purified or unpurified in an acetylene cylinder that is cooled to −20° C. As FIG. 9 illustrates, the fractional concentration of acetone in the dispensed acetylene after passing through the purifier is at 10 ppm or below. FIG. 9 also shows that without the purifier, the acetone concentration increases are more acetylene is consumed from the cylinder. Therefore, the purifier removes the process variability and holds the fractional concentration of acetone at a lower value.

The invention claimed is:

1. A process for providing a high purity acetylene comprising 100 ppm or less solvent to a point of use comprising:
    cooling an acetylene storage vessel comprising acetylene and at least one solvent to a temperature ranging from 0° C. to −35° C.; and
    dispensing acetylene directly from the storage vessel as a high purity fluid acetylene stream to a point of use, wherein the solvent is present at 100 ppm or less in the acetylene stream.

2. The process of claim 1 wherein the at least one solvent is selected from the group consisting of: acetone, dimethyl formamide, N-methylpyrrolidone, and combinations thereof.

3. The process of claim 2 wherein the solvent is dimethylformamide.

4. The process of claim 3 further comprising passing the acetylene and the at least one solvent through at least one purifier prior to the dispensing step.

5. The method of claim 4 wherein the at least one purifier comprises a purifier selected from the group consisting of: activated carbon, a molecular sieve, silica gel, zeolite, and combinations thereof.

* * * * *